(12) United States Patent
Clark

(10) Patent No.: US 8,621,930 B2
(45) Date of Patent: Jan. 7, 2014

(54) TRANSDUCERS

(75) Inventor: Matthew Clark, Nottingham (GB)

(73) Assignee: The University of Nottingham, Nottingham (GB)

( * ) Notice: Subject to any disclaimer, the term of this patent is extended or adjusted under 35 U.S.C. 154(b) by 674 days.

(21) Appl. No.: 12/301,915

(22) PCT Filed: May 24, 2007

(86) PCT No.: PCT/GB2007/001925
§ 371 (c)(1),
(2), (4) Date: Aug. 20, 2009

(87) PCT Pub. No.: WO2007/135439
PCT Pub. Date: Nov. 29, 2007

(65) Prior Publication Data
US 2012/0048020 A1    Mar. 1, 2012

(30) Foreign Application Priority Data
May 24, 2006  (GB) .................................. 0610318.8

(51) Int. Cl.
*G01N 29/24*    (2006.01)

(52) U.S. Cl.
USPC ........................................................ 73/632

(58) Field of Classification Search
USPC ........................................................ 73/632
See application file for complete search history.

(56) References Cited

U.S. PATENT DOCUMENTS

| | | | |
|---|---|---|---|
| 4,121,470 A * | 10/1978 | Kaule ............................. | 73/643 |
| 4,581,939 A | 4/1986 | Takahashi | |
| 6,188,478 B1 | 2/2001 | Fuchs et al. | |
| 2002/0080355 A1 * | 6/2002 | Maris ............................. | 356/432 |
| 2005/0074635 A1 * | 4/2005 | Mitani et al. ............ | 428/694 ST |
| 2005/0241398 A1 | 11/2005 | Suzuki et al. | |

FOREIGN PATENT DOCUMENTS

WO    WO 2007/003952    1/2007

OTHER PUBLICATIONS

Aharoni, a. et al., "Monitoring Material Grain Size by Laser-Generated Ultrasound", Applied Physics Letters, vol. 59, No. 27, Dec. 30, 1991, pp. 3530-3532.
Clark, Matt et al., "Non-Contact Acoustic Microscopy", Measurement Science and Technology, vol. 11, No. 12, Dec. 1, 2000, pp. 1792-1801.
Gostein, M. et al., "Non-Contact Metal Film Metrology Using Impulsive Stimulated Thermal Scattering", AIP Conference Proceedings, No. 550, 2001, pp. 478-488.
Hong, Y. et al., "Rapid and Accurate Analysis of Surface and Pseudo-Surface Waves Using Adaptive Laser Ultrasound Techniques", Ultrasonics, vol. 42, No. 1-9, Apr. 2004, pp. 515-518.
Stratoudaki, T. et al., "Cheap Optical Transducers (CHOTs) for Narrowband Ultrasonic Applications," Measurement Science and Technology, vol. 18, Feb. 5, 2007, pp. 843-851.

* cited by examiner

*Primary Examiner* — Hezron E Williams
*Assistant Examiner* — Gregory J Redmann
(74) *Attorney, Agent, or Firm* — Nixon & Vanderhye P.C.

(57) ABSTRACT

A generator structure has alternating linear regions which are respectively relatively absorbing and relatively non-absorbing. When the structure is illuminated, the spatial contrast in the absorption created by the characteristics of the regions gives rise to mechanical effects within the workpiece, such as localized heating. This results in ultrasound being created to propagate through the workpiece.

17 Claims, 3 Drawing Sheets

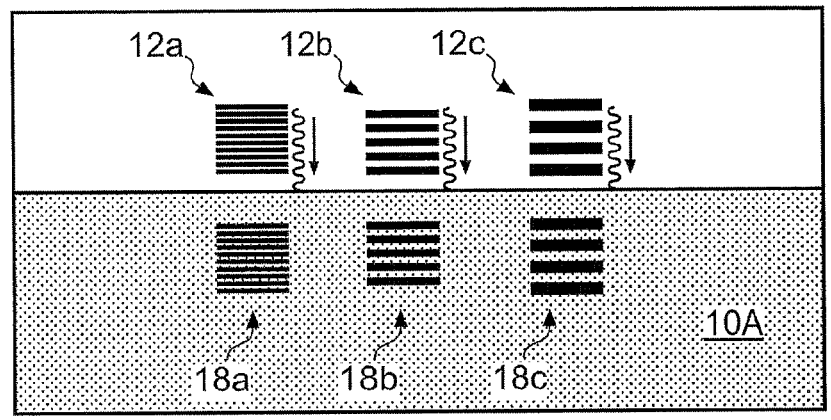
Fig. 5
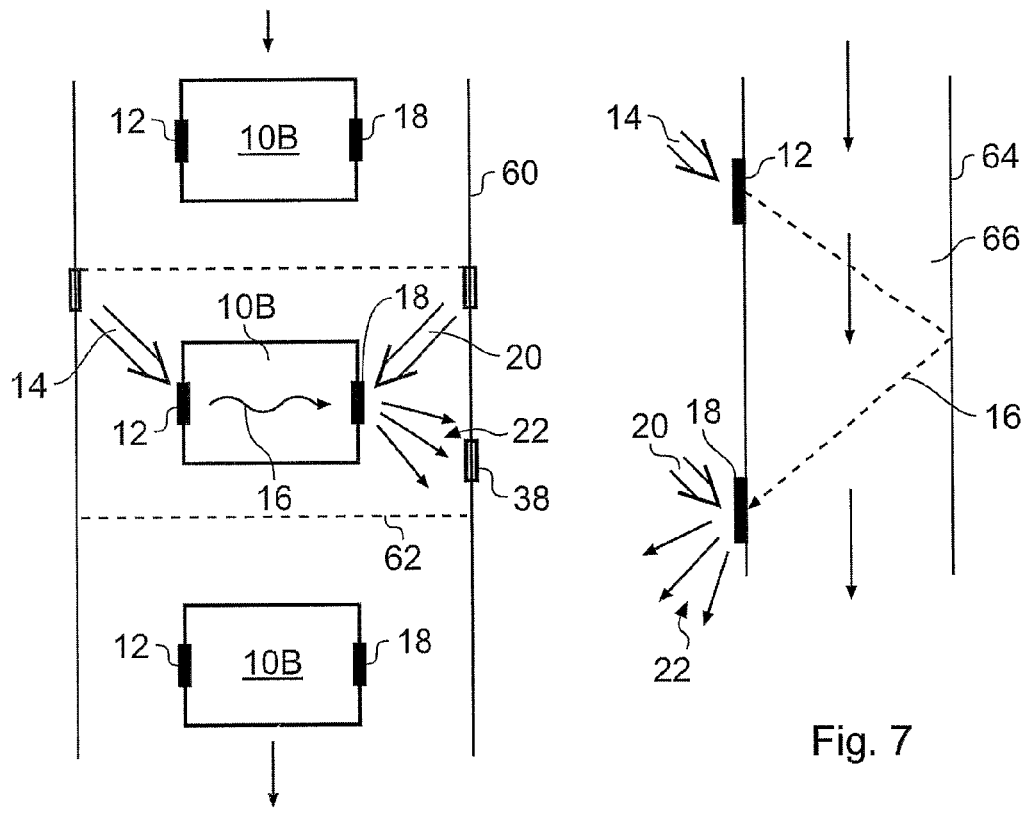
Fig. 6
Fig. 7

TRANSDUCERS

This application is the U.S. national phase of International Application No. PCT/GB2007/001925 filed 24 May 2007 which designated the U.S. and claims priority to Great Britain Patent Application No. 0610318.8 filed 24 May 2006, the entire contents of each of which are hereby incorporated by reference.

The present invention relates to transducers.

Transducers are used for many applications, including applications in non-destructive testing at ultrasonic frequencies. In ultrasonic non-destructive testing, ultrasound is caused to propagate through a workpiece, and is detected. The detected ultrasound can be used to provide information about the workpiece, such as the presence of defects.

Embodiments of the invention provide a transducer for generating ultrasound in a workpiece, comprising:

a structure provided at the workpiece to provide, when illuminated, spatial contrast in the absorption of illumination by the workpiece, whereby to create ultrasound within the workpiece.

The structure may be formed at the surface of the workpiece or within the workpiece. The structure may be formed by modifying the workpiece to create absorption contrast. The material of the workpiece may be modified. Modification may be permanent. Modification may be by etching. The structure may be formed by applying additional material to the workpiece. The additional material may be applied to the surface of the workpiece, or there may be a coupling layer between the structure and the workpiece. The additional material may be applied by printing or by coating or by attachment of a pre-formed structure, which may be self-adhesive. The additional material may be removably applied.

The spatial contrast may be provided by differences in the reflectivity or absorptivity of the workpiece.

The structure may be so formed that, when illuminated, the spatial contrast creates stress in the workpiece. Stress may be created by a thermo-elastic, ablative or electro-strictive mechanism. The structure may be operable to provide spatial contrast when illuminated by electromagnetic radiation, visible light, laser light, microwave or radio illumination.

The structure may have an associated unique identifier, which may be machine-readable.

Embodiments of the invention provide a transducer system comprising a transducer as aforesaid and an illumination system operable, in use, to illuminate the structure.

The illumination system may be operable to provide electromagnetic radiation, visible light, laser light, microwave or radio illumination.

The system may comprise a plurality of transducers carried by respective ones of a group of workpieces which sequentially pass the illumination system for interaction therewith.

The transducer may be associated with a pipe through which fluid flows, the ultrasound passing through the fluid, during use.

Embodiments of the invention provide a workpiece carrying a transducer as aforesaid.

Embodiments of the invention provide a method of generating ultrasound in a workpiece, in which:

a structure is provided at the workpiece to provide spatial contrast, when illuminated, in the absorption of illumination by the workpiece, and the structure is illuminated to create ultrasound within the workpiece.

The structure may be formed at the surface of the workpiece. The structure may be formed by modifying the workpiece to create absorption contrast. The material of the workpiece may be modified. Modification may be permanent. Modification may be by etching. The structure may be formed by applying additional material to the workpiece. The additional material may be applied to the surface of the workpiece, or there may be a coupling layer between the structure and the workpiece. The additional material may be applied by printing or by coating or by attachment of a pre-formed structure, which may be self-adhesive. The additional material may be removably applied.

The spatial contrast may be provided by differences in the reflectivity or absorptivity of the workpiece.

The structure may be so formed that, when illuminated, the spatial contrast creates stress in the workpiece. Stress may be created by a thermo-elastic, ablative or electro-strictive mechanism. The structure may be operable to provide spatial contrast when illuminated by electromagnetic radiation, visible light, laser light, microwave or radio illumination.

A unique identifier, which may be machine-readable, may be associated with the or each structure.

Embodiments of the invention provide a method of non-destructive testing of a workpiece, in which:

ultrasound is generated in the workpiece by the method set out above; and the ultrasound is detected to provide information about the workpiece.

The method of testing may be executed at intervals, there being periods of normal use of the workpiece, between episodes of testing. The structure may remain on the workpiece between testing episodes.

Embodiments of the invention provide a transducer for detecting ultrasound in a workpiece, comprising:

a structure provided at the workpiece to be illuminated, during use, the structure interacting, in use, with the ultrasound to provide detectable modulation of the illumination.

The structure may be formed at the surface of the workpiece or within the workpiece. The structure may be formed by modifying the workpiece. The material of the workpiece may be modified. Modification may be permanent. Modification may be by etching. The structure may be formed by applying additional material to the workpiece, or there may be a coupling layer between the additional material and the workpiece. The additional material may be applied to the surface of the workpiece. The additional material may be applied by printing or by coating or by attachment of a pre-formed structure, which may be self-adhesive. The additional material may be removably applied.

The structure may be provided by differences in the reflectivity, absorptivity or phase contrast of the workpiece.

The structure may have an associated unique identifier, which may be machine-readable.

The workpiece surface may be modified to create elements which together form a grating structure which provides modulation when ultrasound passes through the workpiece in the region of the elements. The elements may change in size, relative size, position or relative position in response to ultrasound passing through. The elements may together form a reflective grating. The grating structure may provide modulation within the orders of illumination diffracted by the grating, when ultrasound passes.

Embodiments of the invention provide a transducer system comprising a transducer as aforesaid, an illumination system operable, in use, to illuminate the structure, and a sensor arrangement operable to detect modulation of the illumination.

Embodiments of the invention provide a workpiece carrying a transducer as aforesaid.

Embodiments of the invention provide a method of detecting ultrasound in a workpiece, in which:

a structure is provided at the workpiece, an illumination system is provided to illuminate the structure, during use, the structure interacting, in use, with ultrasound in the workpiece, to provide detectable modulation of the illumination, and a sensor arrangement operable to detect modulation of the illumination.

Embodiments of the invention provide a method of non-destructive testing of a workpiece, in which:

ultrasound is generated in the workpiece, and the ultrasound is detected by the method set out above, to provide information about the workpiece.

The method of testing may be executed at intervals, there being periods of normal use of the workpiece, between episodes of testing. The structure may remain on the workpiece, between testing episodes.

Embodiments of the invention provide a system for non-destructive testing of a workpiece, comprising:

a transducer for generating ultrasound, of the type defined above, and a transducer for detection of ultrasound, of the type defined above.

Embodiments of the invention provide a method of non-destructive testing of a workpiece, in which ultrasound is generated by a transducer of the type defined above; and is detected by a transducer of the type defined above.

The method of testing may be executed at intervals, there being periods of normal use of the workpiece, between episodes of testing. The transducer structures may remain on the workpiece between testing episodes.

Embodiments of the present invention will now be described in more detail, by way of example only, and with reference to the accompanying drawings, in which:

FIG. 5 is a plan view of alternative generator and detector structures for use in the method;

FIG. 6 illustrates an embodiment of the invention in use with sequentially passing workpieces; and FIG. 7 illustrates an embodiment of the invention in use with a pipe through which fluid is flowing.

OVERVIEW

Figure 1:
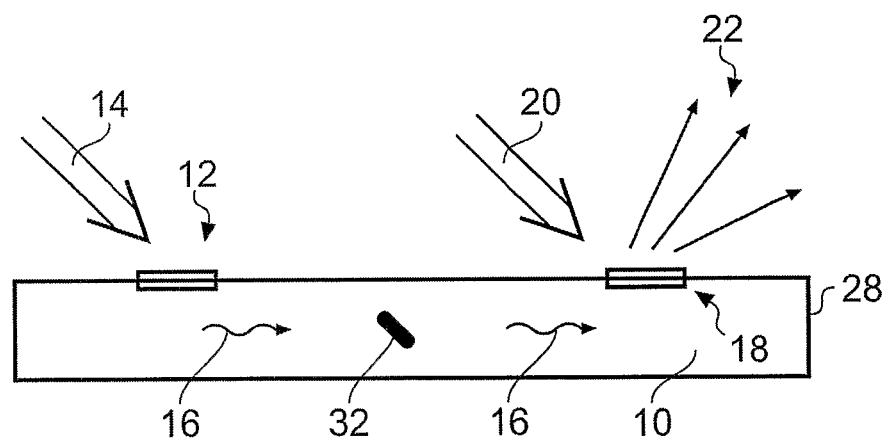
FIG. 1 is a highly schematic section through a workpiece, indicating a method of non-destructive testing in accordance with one embodiment of the invention.

FIG. 1 illustrates a workpiece 10 in which ultrasound is generated and detected, for example for non-destructive testing purposes. A generator structure 12, to be described in more detail below, is provided at the workpiece 10 to provide, when illuminated, spatial contrast in the absorption of illumination 14 by the workpiece 10. This creates ultrasound 16 within the workpiece 10.

A detector structure 18, to be described in more detail below, is provided at the workpiece 10 and is illuminated at 20, during use. The detector structure 18 interacts, in use, with the ultrasound 16 to provide detectable modulation of the illumination 20, indicated generally at 22.

In this specification, the term ultrasound is used in relation to elastic waves with frequencies above about 20 kHz, and includes all wavemodes of elastic wave, such as Rayleigh waves, longitudinal, shear, Love and Lamb waves, surface acoustic waves (SAWs), leaky SAWs, and surface skimming bulk waves (SSBWs).

Generator

Figure 2A:
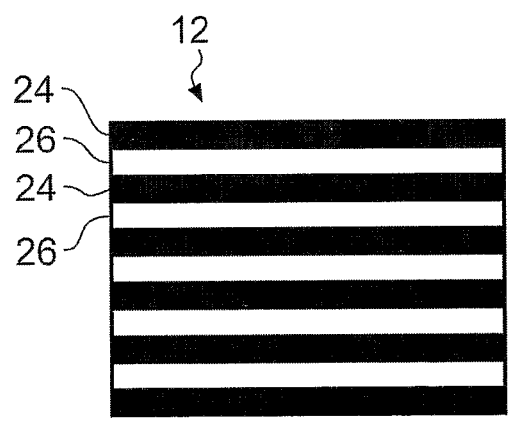
FIGS. 2A and 2B are plan and section views of generator structures used in the method of FIG. 1.
Figure 2B:
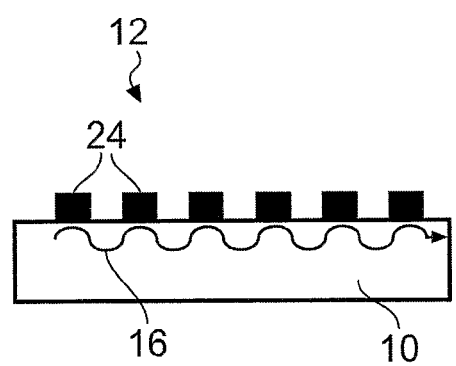

The generator structure 12 is illustrated in more detail in FIGS. 2A and 2B. The generator structure 12 has alternating linear regions 24, 26. The regions 24 are relatively absorbing of the illumination 14. The regions 26 are relatively non-absorbing of the illumination 14.

The difference in the absorption characteristics of the regions 24, 26 may be created in many different ways. For example, the material of the workpiece 10 may be modified at or near its surface, to create absorption contrast. This may be by increasing the reflectivity of regions 26, or by decreasing the reflectivity of regions 24, or by increasing the absorption characteristics of regions 24, or by decreasing the absorption characteristics of regions 26. Etching may be used to create the absorption contrast.

The regions 24, 26 may be formed within the body of the workpiece 10, if the material of the workpiece, and the nature of the illumination are such as to provide the absorption contrast.

In other examples, the structure 12 may be formed by applying additional material to the workpiece 10, preferably at the surface. This may be applied as a coating, as illustrated in FIG. 2B, in which areas 24 are formed by additional material deposited either directly on the surface 28 of the workpiece 10, as shown, or over a coupling layer (not shown) between the structure 12 and the surface of the workpiece 10. The additional material may be deposited by a coating technique, a printing technique or by attachment of a pre-formed structure, which may be in the form of a structure pre-formed on a self-adhesive substrate, for attachment to the workpiece 10. The method of attachment may be removable, to allow the structure 12 to be re-used at a different location on the same or another workpiece, or to be disposable. The structure 12 may be covered with a layer providing protection and/or retention.

When the generator structure 12 is illuminated at 14, the spatial contrast in the absorption of the illumination 14 by the workpiece 10 gives rise to mechanical effects within the workpiece 10. For example, the absorption of the illumination 14 may give rise to localised heating within the workpiece 10, there being a spatial variation in the localised heating, by virtue of the form of the structure 12. This creates expansion of the workpiece 10, which is not uniform across the workpiece 10. Accordingly, strong, pulsed illumination 14, such as from a laser, can create rapid, localised expansion in the regions 24. This creates mechanical disturbance within the workpiece 10, which results in ultrasound 16 being created to propagate through the workpiece 10.

Other mechanisms may contribute to the creation of the ultrasound 16, such as thermo-elastic, ablative or electrostrictive mechanisms. The effective mechanism will vary according to the material chosen for the workpiece, the nature of the generator structure 12, and the nature of the illumination.

The type of the illumination 14 can be selected according to the material of the workpiece 10 and the mechanism for absorption. The illumination 14 is envisaged to be a form of electromagnetic radiation, which may be visible light, such as laser light, or may be microwave or radio illumination.

The generator structure 12 and the illumination system 14a, including a source of the chosen type of illumination, together form a transducer system. In use, the illumination source 14a is used to illuminate the generator structure 12. This creates spatial contrast in the absorption of the illumination 14 by the workpiece 10, which in turn creates ultrasound by virtue of the absorption mechanisms described.

The ultrasound created from the generator structure 12 propagates through the workpiece 10, possibly encountering one or more faults 32 within the body of the workpiece 10, until reaching the detector structure 18.

Detector

Figure 3:
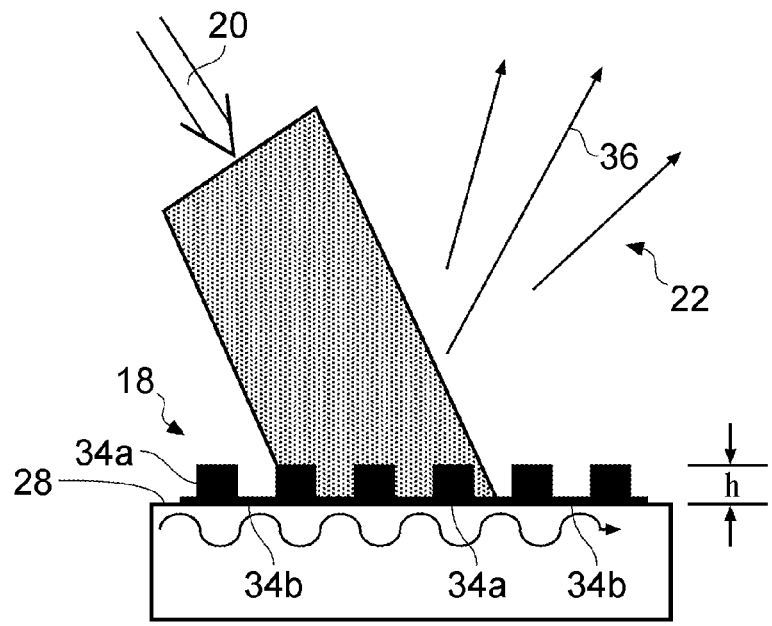
FIG. 3 is a section of a detector structure used in the method of FIG. 1.

The detector structure 18 is illustrated in more detail in FIG. 3.

The detector structure 18 is formed, in this example, as a grating structure. The structure 18 is provided at the surface of the workpiece 10 and is therefore mechanically disturbed by the passage of ultrasound 16 through the workpiece 10, in the vicinity of the structure 18. This disturbance of the detector structure 18 is used to provide detectable modulation of the illumination 20, as will be described below.

In the example illustrated in FIG. 3, the structure 18 is formed by applying additional material to the workpiece 10, preferably at the surface. This may be applied by a coating technique, as illustrated in FIG. 3, in which elongate regions 34A are formed by additional material deposited either directly on the surface 28 of the workpiece 10, as shown, or over a coupling layer (not shown) between the structure 12 and the surface of the workpiece 10. The additional material may be deposited by a coating technique, a printing technique or by attachment of a pre-formed structure, which may be in the form of a structure pre-formed on a self-adhesive substrate, for attachment to the workpiece 10. The method of attachment may be removable, to allow the structure 18 to be re-used at a different location on the same or another workpiece, or to be disposable.

The regions 34A are separated by elongate regions 34B. The resulting surface profile has regions 34A raised above regions 34B, as can be seen from FIG. 3. The steps formed between the regions 34A, 34B alter the complex reflectivity between the regions by introducing a phase shift in the illumination 20.

This change in reflectivity may alternatively be achieved by changing the absorption or reflection coefficients of the regions 34A, 34B. The contrast between the regions 34A, 34B may be achieved by etching, printing, machining, laser marking or other techniques.

As an alternative to a phase grating, an amplitude grating could be used. An amplitude grating may be formed, for example, by providing contrast in the absorption or reflection characteristics of the regions 34A, 34B.

The regions 34A, 34B may be formed within the body of the workpiece 10, if the material of the workpiece, and the nature of the illumination are such as to provide the absorption, reflection or phase contrast.

In this example, the detector structure 18 is illuminated at 20 by incident laser illumination. This reflects from the grating structure 18 as a diffracted beam 36, having various diffraction orders as illustrated by arrows in FIG. 3. When ultrasound 16 passes the grating structure 18, the size, relative size, position or relative position of the elements 34A, 34B forming the grating structure 18 will change in response to the ultrasound 16, which will in turn cause changes in the diffracted beam 36. In particular, the height h (FIG. 3) of the grating elements 34A will change in response to the ultrasound 16. The grating height h is a factor determining the energy distribution between the various orders of the diffracted beam 36. Accordingly, the interaction of the grating structure 18 with the ultrasound 16 results in a change of the distribution of energy among the diffraction orders. This modulation can be observed by an appropriate sensor 38, for example by observing a selected order of the diffracted beam 36.

For example, the zero order of the diffracted beam 36 may be chosen for observation. It can be shown that if the height h corresponds to one eighth of the optical wavelength, 50% of the energy of the illumination 20 will be directed to the zero order. The strength of the zero order will then change, i.e. be modulated, as the grating height changes upon interaction with the ultrasound 16.

The sensor 38 may be a photo-diode forming, with the detector structure 18 and the illumination source 30, a transducer system for detecting the modulation of the illumination 20 arising from interaction with the ultrasound 16, at the grating.

It is to be particularly noted that the zero order of the diffracted beam 34 arises from direct specular reflection. Accordingly, the direction of the zero order does not change as a result of modulation, thus simplifying the requirements for monitoring the diffracted beam 36 by the sensor 38.

System

Figure 4:
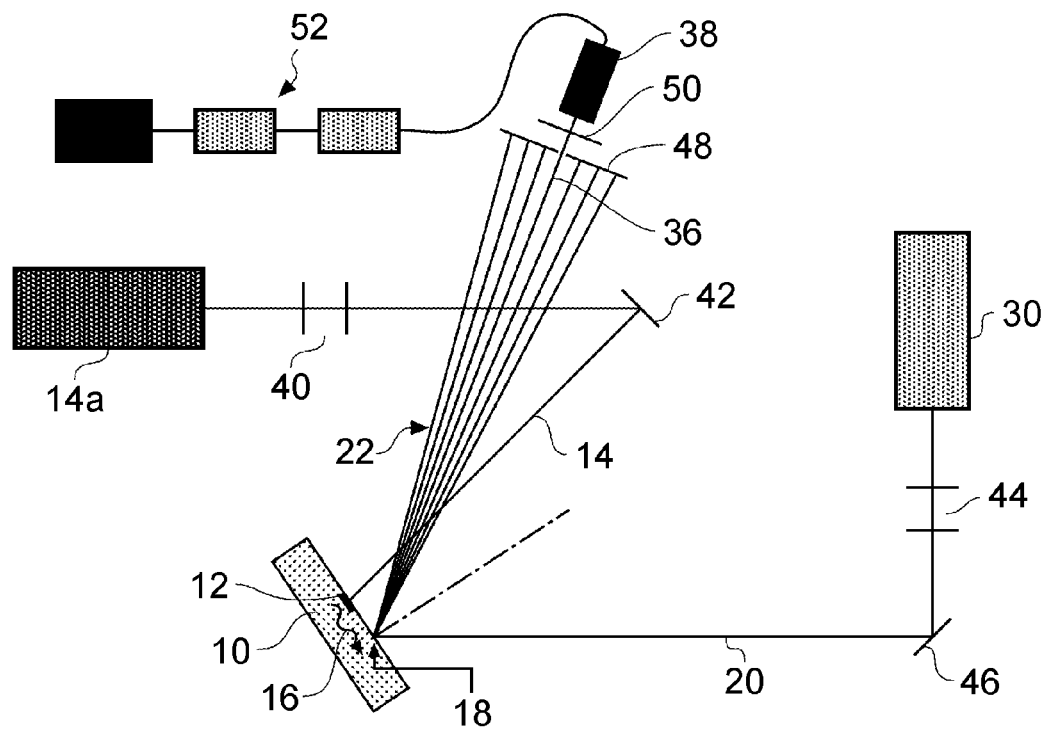
FIG. 4 is a schematic diagram of the complete system used for the method of FIG. 1.

FIG. 4 illustrates the two transducer systems in more detail. Many features illustrated in FIG. 4 correspond with features described above and are therefore given the same reference numerals. In the arrangement of FIG. 4, the workpiece 10 carries a generator structure 12 and a detector structure 18 at its surface. The illumination source 14A for the structure 12 is in the form of a q-switched Nd:YAG laser emitting at 1064 nm with a pulse duration of 20 ns. This type of laser is readily available, on a commercial basis.

In this example, the output of the laser 14a passes through a beam expanding system 40 and may be directed to the generator structure 12 by a mirror 42, if required.

Pulses from the laser 14a create ultrasound 16 within the workpiece 10, as has been described. These travel through the workpiece 10 towards the detector structure 18, and may encounter faults 32.

The detector structure 18 is illuminated by the source 30 which is, in this example, a HeNe laser emitting at 633 nm. This type of laser is readily available, on a commercial basis. Accordingly, for this example, the height h of the grating elements 34A is chosen as approximately 79 nm, to be one eighth of the optical wavelength. The emission of the laser 30 passes through a second beam expanding system 44, in this example, and may be directed by a second mirror 46, if required, to illuminate the detector structure 18. The diffracted beam 36 illuminates an iris 48 which separates out the zero order of the diffracted beam 36 to illuminate the sensor 38, through an optional lens system 50. The output of the photo-diode sensor 38 is applied to circuits 52 for signal treatment and analysis. In particular, the intensity of the zero order of the diffracted beam 36 is observed to recover information about the modulation provided within the detector structure 18 by the interaction with ultrasound 16.

Selection Characteristics

It can be shown that the bandwidth of the generated ultrasound 16 is set by the number of elements of the generator structure which are contributing to the effects, that is, the number of elements being illuminated. Increasing the number of illuminated elements reduces the bandwidth of the created ultrasound 16.

At the detector structure 18, the grating form of the structure 18 results in the ultrasound 16 being filtered, so that the modulation in the diffracted beam 36 arises from the ultrasound 16 as filtered by the grating structure 18. It can be shown that the detection bandwidth of the structure 18 becomes narrower as the number of grating elements increases.

In both cases, the grating spacing allows for frequency selection.

The mode of the ultrasound generated in the structure 12 is influenced by the form of the structure 12, as has been described. In the examples described above, the structures 12 have been line gratings. Other forms of gratings could be used. For example, circular gratings could be used. Changing the shape of the grating elements forming the structures 12, 18 allows different modes of ultrasound propagation to be stimulated and detected within the workpiece 10, thus allowing additional information to be recovered in relation to the workpiece 10. It is envisaged that appropriate design of the structures 12, 18 will allow substantially any desired wavemode of elastic wave to be generated and detected, such as Rayleigh waves, longitudinal, shear, Love and Lamb waves, SAWs, leaky SAWs and SSBWs.

The form of the structures 12, 18 also affects their directional selectivity, allowing testing to be carried out in preferred directions chosen by appropriate orientation of the structures.

Accordingly, appropriate selection of the dimensions of the structures 12, 18 allows the frequency and bandwidth of ultrasound generation and ultrasound detection to be controlled, each factor being controllable substantially independently of the others.

Multiple Transducers

The frequency and bandwidth behaviour can be used in a manner illustrated in FIG. 5, which illustrates the surface of a workpiece 10A. The surface of the workpiece 10A is provided with three generator structures 12A 12B, 12C and three detector structures 18A, 18B, 18C. It can be seen from FIG. 5 that the dimensions of the elements forming the structures 12A, 18A are relatively fine, the dimensions of the structures 12C, 18C are relatively coarse, and the dimensions of the structures 12B, 18B are intermediate those of the structures 12A, 12C, 18A, 18C.

In one example, we have formed a workpiece 10A having structures 12A, 18A formed to operate at 20 MHz, structures 12B, 18B formed to operate at 10 MHz and structures 12C, 18C formed to operate at 5 MHz. Many other frequencies and combinations of frequencies could be chosen, as could the number of pairs of structures 12, 18.

The provision of multiple structures 12, 18, in the manner of FIG. 5, allows ultrasound to be generated and detected at multiple frequencies, either simultaneously by illuminating more than one generator structure, and the corresponding detector structures, or selectively, by illuminating a selected generator structure and the corresponding detector structure. At each of the frequencies in use, bandwidth in the generation and detection can be controlled, and frequency, mode and direction can be selected, by using the effects described above. This, for example, allows the workpiece 10 to be tested at various different ultrasound frequencies 16, allowing more information to be recovered about the state of the workpiece 10.

Sequential Workpieces

FIG. 6 schematically illustrates how the principles and examples described above can be applied for non-destructive testing of a plurality of workpieces. For example, the workpieces 10B of FIG. 6 may be manufactured items passing along a path 60, for example as part of a manufacturing process. Each workpiece 10B is provided with a generator structure 12 and a detector structure 18. In this example, the structures 12, 18 are positioned on opposite faces of the workpieces 10B.

An illumination source 14 is provided at a position along the path 60, so that the workpieces 10B will sequentially pass the source 14, as they move along the path 60. An illumination source 20 is also provided, generally at the same region of the path 60 as the source 14. A sensor 38 is also provided in the region of the source 20. The illumination sources 14, 20 and the sensor 38 are arranged so that each workpiece 10B will sequentially arrive at a test station illustrated at 62, at which the generator structure 12 is illuminated by the source 14, to create ultrasound within the workpiece 10B. The ultrasound 16 passes through the workpiece 10B. The detector structure 18 is also illuminated, by the source 20, so that the sensor 38 is able to observe the modulation provided by the ultrasound received at the detector structure 18, as has been described. Accordingly, each workpiece 10B can be individually tested in this non-destructive manner, with appropriate action being taken in response to a finding of abnormal modulation sensed at the sensor 38, indicative of an abnormality within the workpiece 10B.

In one example, the workpieces 10B may be containers of a foodstuff. For example, they may contain milk or other dairy product. We envisage that changes within foodstuffs, as they lose freshness, will give rise to detectable changes in behaviour under the ultrasound testing which has been described. Accordingly, freshness of the contents of each container 10B can be assessed individually. Containers with contents which are not fresh can be rejected.

It is envisaged that each workpiece 10B can also be provided with a machine-readable code, such as a bar code, there being an appropriate reading arrangement provided in the path 60, preferably in the region of the test station 62. This allows each test result to be associated with the unique identifier of the corresponding workpiece 10B, providing a test record specific to the particular workpiece 10B.

Pipelines

The arrangements described in relation to FIG. 6 relate to individual testing of discrete items. In a further example, illustrated in FIG. 7, continuous testing is provided for material flowing along a pipe 64, which may be conveying a foodstuff. In this example, a generator structure 12 is provided on the wall of the pipe 64 to create ultrasound 16 within the bore 66 of the pipe 64, when illuminated at 14. A detector structure 18 is provided on the wall of the pipe 64, to detect the ultrasound 16 when illuminated at 20, to provide a modulated, reflected beam 22. This arrangement allows continuous monitoring of the material flowing through the pipe 64, so that appropriate action can be taken in the event that an unacceptable change is detected, which might arise from lack of freshness of a foodstuff, incorrect processing or formulation in a prior processing step, or the like.

Periodic Testing

The workpieces 10B of FIG. 6 are described as carrying generator structures and detector structures. Accordingly, they can be tested again, at any time, by provision of appropriate illumination and sensor arrangements. In the case of foodstuffs, for example, they could be tested at various stages of production, delivery and storage, providing a consistent set of data from which the current freshness or other condition of the contents can be assessed.

This principle of periodic testing of a workpiece can also be used in relation to other types of workpiece, such as components of a machine. Any component which requires periodic testing can be provided with a generator structure 12 and a detector structure 18 at an appropriate position. The structures 12, 18 create negligible disturbance to the workpiece 10, being surface formations. Thus, the structures 12, 18 may remain in place during periods of normal use of the workpiece. At intervals, the structures 12, 18 may be used to generate and detect ultrasound within the workpiece, to provide a non-destructive test result relating to the performance and/or condition of the workpiece. Since the structures 12, 18 can remain on the test piece between testing episodes, each testing episode is consistently executed, so that the results of the periodic testing episodes can be related to each other, without additional calibration being required.

Remote Testing and In Situ Testing

In the arrangements described, the generator and detector structures are illuminated. Illumination of the complete structure 12 or 18 is required. It is envisaged that this will be possible, in many applications, by using an illumination source which is remote from the structure 12, 18. This facilitates testing in hostile environments, or within operating machines, for example. Continuous testing, within an operating environment, is also envisaged.

Other Materials

Various references have been made above to foodstuffs. Other materials could be tested, such as chemical products, drugs, human or animal tissue or any other material which supports elastic waves. Materials in liquid, solid or gas phase can be tested.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A transducer for generating ultrasound in a workpiece of a material in which mechanical disturbance is created by absorption of illumination, comprising:
   a structure provided at the workpiece, wherein the structure is formed at a surface of the workpiece or within the workpiece, and wherein the structure is formed by modifying the workpiece to create spatial contrast in the ability of the workpiece to absorb illumination, in use, and further comprising an illumination system operable, in use, to illuminate the structure with pulsed laser illumination, wherein the pulsed laser illumination creates, in use, spatial contrast in the mechanical disturbance within the workpiece when illuminated, to create ultrasound within the workpiece.

2. A transducer according to claim 1, wherein modification is by etching.

3. A transducer according to claim 1, wherein the structure has an associated unique identifier.

4. A transducer system comprising a transducer according to claim 1, comprising a plurality of transducers carried by respective ones of group of workpieces which sequentially pass the illumination system for interaction therewith.

5. A transducer system comprising a transducer according to claim 1, wherein the transducer is associated with a pipe through which fluid flows, the ultrasound passing through the fluid, during use.

6. A transducer according to claim 1, wherein the structure is provided by differences in the reflectivity or absorptivity of the workpiece.

7. A transducer according to claim 1, wherein the structure is so formed that, when illuminated, the spatial contrast creates stress in the workpiece.

8. A transducer according to claim 7, wherein stress is created by a thermo-elastic, ablative or electro-strictive mechanism.

9. A transducer according to claim 1, wherein the structure is operable to provide spatial contrast when illuminated by electromagnetic radiation, visible light, laser light, microwave or radio illumination.

10. A method of generating ultrasound in a workpiece of a material in which mechanical disturbance is created by absorption of illumination, in which:
    a structure according to claim 1 is provided at a location chosen from the surface of the workpiece and within the workpiece, by modifying the workpiece to provide spatial contrast in the ability of the workpiece to absorb illumination,
    and the structure is illuminated with pulsed laser illumination, wherein the pulsed laser illumination creates spatial contrast in the mechanical disturbance within the workpiece, to create ultrasound within the workpiece.

11. A method according to claim 10, wherein the spatial contrast is provided by differences in the reflectivity or absorptivity of the workpiece.

12. A method according to claim 10, wherein the structure is so formed that, when illuminated, the spatial contrast creates stress in the workpiece.

13. A method according to claim 12, wherein stress is created by a thermo-elastic, ablative or electro-strictive mechanism.

14. A method according to claim 10, wherein the structure is operable to provide spatial contrast when illuminated by electromagnetic radiation, visible light, laser light, microwave or radio illumination.

15. A method of non-destructive testing of a workpiece, in which:
    ultrasound is generated in the workpiece by the method of claim 10; and
    the ultrasound is detected to provide information about the workpiece.

16. A method according to claim 15, wherein the method of testing is executed at intervals, there being periods of normal use of the workpiece, between episodes of testing.

17. A method according to claim 16, wherein the structure remains on the workpiece between testing episodes.

* * * * *